(12) United States Patent
Baskin et al.

(10) Patent No.: US 6,175,760 B1
(45) Date of Patent: Jan. 16, 2001

(54) LESION LOCALIZER FOR NUCLEAR MEDICINE

(75) Inventors: Kevin M. Baskin; William H. Barnhart, both of Iowa City, IA (US)

(73) Assignee: University of Iowa Research Foundation, Iowa City, IA (US)

(*) Notice: Under 35 U.S.C. 154(b), the term of this patent shall be extended for 0 days.

(21) Appl. No.: 09/025,056

(22) Filed: Feb. 17, 1998

(51) Int. Cl.[7] ............................................. A61B 6/00
(52) U.S. Cl. .......................... 600/436; 600/431; 600/7; 606/116
(58) Field of Search ................................ 600/436, 1, 3, 600/4, 5, 7, 431; 606/130, 96, 108, 116; 604/16, 60, 93

(56) References Cited

U.S. PATENT DOCUMENTS

| | | | |
|---|---|---|---|
| 2,269,458 | 1/1942 | Kahn | 250/106 |
| 3,674,006 | * 7/1972 | Holmer . | |
| 3,811,426 | * 5/1974 | Culver et al. . | |
| 4,086,914 | * 5/1978 | Moore . | |
| 4,096,862 | 6/1978 | DeLuca | 128/348 |
| 4,402,308 | * 9/1983 | Scott . | |
| 4,616,656 | 10/1986 | Nicholson et al. | 128/630 |
| 4,627,420 | * 12/1986 | Katz . | |
| 4,781,198 | 11/1988 | Kanabrocki | 128/654 |
| 4,787,384 | 11/1988 | Campbell et al. | 128/330 |
| 4,787,391 | 11/1988 | Elefteriades | 128/654 |
| 4,815,449 | * 3/1989 | Horowitz . | |
| 4,861,520 | * 8/1989 | Van't Hooft et al. . | |
| 4,957,476 | * 9/1990 | Cano . | |

(List continued on next page.)

FOREIGN PATENT DOCUMENTS

| | | |
|---|---|---|
| 3937 052 A 1 | 5/1990 | (DE) . |
| 2 686 499 | 7/1993 | (FR) . |
| WO 94/17722 | 8/1994 | (WO) . |

\* cited by examiner

*Primary Examiner*—Marvin M. Lateef
*Assistant Examiner*—Shawna J Shaw
(74) *Attorney, Agent, or Firm*—Woodard, Emhardt, Naughton, Moriarty & McNett (57) ABSTRACT

An apparatus and method for marking the location for excising a bone lesion by surgery. A localizing needle containing radioactive source of radiation at its tip, is received in a guide needle, with sharp ends of both needles juxtaposed. A cable extends from the opposite end of the localizing needle through the guide needle lumen and out the proximal end of the guide needle. With the bone lesion visualized on a monitor in real time, the needle combination is inserted, tip-first, through the skin and advanced toward the lesion. The radiation from the localizing needle tip assists the surgeon to manipulate the guide needle tip to a marker site on the bone immediately adjacent the lesion. The guide needle tip is pushed into and securely held in the bone. In one embodiment, a handle secured to the cable outside the proximal end of the guide needle is rotated a quarter turn to anchor hooked tips of the localizing needle in the bone. In the preferred embodiment, the localizing needle is withdrawn from the guide needle, followed by insertion of a starter hole drilling stylet. Following completion of the starter hole in the bone, while the guide needle is still held with its point securely located in the bone, the starter hole drill is withdrawn. Upon entry of the screw tip of the localizing needle in the starter hole, a needle driver received in the guide tube, with handle outside, is rotated, with an interfitting coupling transmitting torque from the handle to the localizing needle to screw it into the bone. After positional verification on the monitor, the needle driver and guide needle are removed from the body and from the cable. The cable portion protruding outside the body is taped to the skin, thereby marking the entry location for subsequent surgery to treat or remove the lesion.

21 Claims, 6 Drawing Sheets

U.S. PATENT DOCUMENTS

| | | | |
|---|---|---|---|
| 4,969,863 | * | 11/1990 | Van't Hooft et al. . |
| 5,037,426 | * | 8/1991 | Goble et al. . |
| 5,154,179 | | 10/1992 | Ratner ............................... 128/653.4 |
| 5,183,455 | * | 2/1993 | Hayman et al. . |
| 5,195,526 | | 3/1993 | Michelson ............................ 128/654 |
| 5,199,939 | | 4/1993 | Dake et al. ................................ 600/3 |
| 5,221,269 | | 6/1993 | Miller et al. ......................... 604/281 |
| 5,234,426 | * | 8/1993 | Rank et al. . |
| 5,282,781 | | 2/1994 | Liprie ........................................ 600/3 |
| 5,320,100 | | 6/1994 | Herweck et al. ..................... 128/654 |
| 5,361,766 | | 11/1994 | Nichols et al. ....................... 128/654 |
| 5,399,868 | * | 3/1995 | Jones et al. . |
| 5,409,004 | | 4/1995 | Sloan .................................... 128/657 |
| 5,425,733 | * | 6/1995 | Schmieding . |
| 5,429,617 | | 7/1995 | Hammersmark et al. ........... 604/264 |
| 5,540,659 | * | 7/1996 | Teirstein . |
| 5,591,207 | * | 1/1997 | Coleman . |
| 5,595,193 | * | 1/1997 | Walus et al. . |
| 5,606,981 | | 3/1997 | Tartacower et al. .................. 128/772 |
| 5,626,613 | | 5/1997 | Schmieding ......................... 606/232 |
| 5,647,374 | | 7/1997 | Cutrer .................................. 128/749 |
| 5,662,111 | * | 9/1997 | Cosman . |
| 5,665,092 | | 9/1997 | Mangiardi et al. ..................... 606/86 |
| 5,682,890 | * | 11/1997 | Kormos et al. . |
| 5,687,739 | | 11/1997 | McPherson ......................... 128/754 |
| 5,772,594 | * | 6/1998 | Barrick . |
| 5,800,445 | * | 9/1998 | Ratcliff et al. . |
| 5,810,841 | * | 9/1998 | McNeirney et al. . |
| 5,853,366 | * | 12/1998 | Dowlatshahi . |
| 5,868,673 | * | 2/1999 | Vesely . |

LESION LOCALIZER FOR NUCLEAR MEDICINE

TECHNICAL FIELD OF THE INVENTION

The present invention relates to medical devices for marking locations for subsequent surgery. Particularly, the invention relates to a localizing device utilizing nuclear medicine imaging.

BACKGROUND OF THE INVENTION

It is well known that cancer is a deadly disease. Early detection and treatment are essential to improving a patient's ability to avoid life-threatening complications and to maximize their chances of survival. One such method of early detection involves non-invasive examination of the patient to identify lesions. As these lesion areas may include cancerous or other diseased tissue, once detected they can be surgically removed.

When radiograms or X-rays are used to locate lesions, as in periodic mammogram screens for breast cancer, a guidewire, needle, or similar device can be placed in the tissue as close as possible to the lesion so that the lesion location may be identified during subsequent surgery. As the localizing device and the lesion itself are both visible to radiograms and X-rays, the relative location of the lesion with respect to the localizing device can be determined by examining a radiograph of the lesion site with the localizing device inserted. However, since it is normally impossible to distinguish lesion tissue from normal healthy tissue by sight or feel, and the radiograph is not always available or usable during surgery, the surgeon must rely only on the localizing device and the earlier radiogram to determine the lesion site during surgery. Accurate determination of the location of the lesion from the localizing device allows the surgeon to approach the site accurately, remove a relatively small amount of tissue and yet still be confident that all the lesion tissue is removed. Several devices have been directed toward increasing the accuracy of localizer placement with respect to the lesion site. For example, inventions to more securely anchor the localizing device in the tissue to prevent inadvertent localizer movement prior to surgery are disclosed in U.S. Pat. Nos. 4,616,656 to Nicholson et al. and 5,221,269 to Miller et al. Additionally, a device which incorporates radiopaque markings at predetermined positions along the axial length of the localizer to further assist in identifying the relative location of the lesion is disclosed in U.S. Pat. No. 5,409,004 to Sloan.

However, many lesions are undetectable through radiographic means due to their depth in the tissue or their proximity to bone material. In these cases, alternative detection means are necessary. One such recently developed alternative involves inoculating the patient with a radioactive isotope which preferentially absorbs in lesion tissue. The presence of the radioactive isotope in the lesions makes the lesion visible to nuclear medicine scans.

One limitation generally associated with the prior art localizing devices is that they are insufficiently visible for use with the localizing techniques developed for nuclear medicine scanning. Another limitation of the prior art localizing devices is that they are limited for use in soft tissue material, such as female breast tissue.

SUMMARY OF THE INVENTION

One aspect of the present invention contemplates an apparatus including a radioactive capsule capable of being anchored in bone as a marker for subsequent surgery. Another aspect of the present invention contemplates a method of localizing lesions in hard tissue by installing a radioactive marker securely in bone adjacent the lesion and which has a cable extending from the marker to the exterior of the patient's skin to identify an entry site for subsequent surgery to remove the lesion. The method includes placement of a localizing marker needle with a radiation source imbedded near its distal point, and a flexible cable extending from its proximal end, inside a guide needle. The guide needle with the localizing needle so-installed, is introduced through the patient's skin and observed on a radiation persistence scope, displaying the lesion, which is visible on the scope due to an accumulation of a radioactive isotope in the lesion. The guide needle with the localizing needle therein is advanced with the help of the imaging scope to a point of contact of a needle with the bone adjacent the lesion. According to a method with one embodiment of the invention, the localizing needle has helical hooks at its distal end and, with the guide needle held against the bone, and a torque applying handle connected to the proximal end of the cable, the cable is turned to screw the hooks into the bone. Then the torque-applying handle is removed from the cable, the guide needle is removed, and the portion of the cable outside the body is taped to the skin to be readily located when the patient is moved to a site for subsequent surgery. According to the preferred embodiment of the invention, the localizing needle has a screw threaded point. After locating the threaded point on the bone adjacent the lesion, and then holding the point of the guide needle securely on the bone adjacent the lesion, the localizing needle is withdrawn from the guide needle. Then a sharp-pointed T-handled drill shaft is inserted through the guide needle to the bone and turned to drill a starter hole in the bone. Then the drill is removed, and the localizing needle re-inserted and the sharp, screw-threaded tip thereof is inserted into the starter hole. A needle driver releasably coupled to the proximal end of the localizing needle and having a handle portion extending outside of the guide needle, is engaged with and used to rotate and thereby drive the screw tip of the localizing needle into the bone for anchorage thereof. When the stability and accuracy of location of the localizing needle relative to the lesion are observed in the scope, the needle driver is removed and the guide needle is removed and the portion of the cable protruding from the skin is then taped to the skin for marking the entrance location for subsequent surgery.

The primary object of the present invention is to provide apparatus and method for providing accurate localization prior to treatment, of sites for surgery or other treatment for bony lesions detectable by radionuclide imaging prior to surgery or other treatment.

DETAILED DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended. Such alterations and further modifications in the illustrated device, and such further applications of the principles of the invention as illustrated therein being contemplated as would normally occur to one skilled in the art to which the invention relates.

The present invention relates generally to an improved method of localizing lesions in hard tissue by inserting a radioactive capsule into the patient and anchoring it in the bone or other hard tissue near the lesion.

Figure 1:
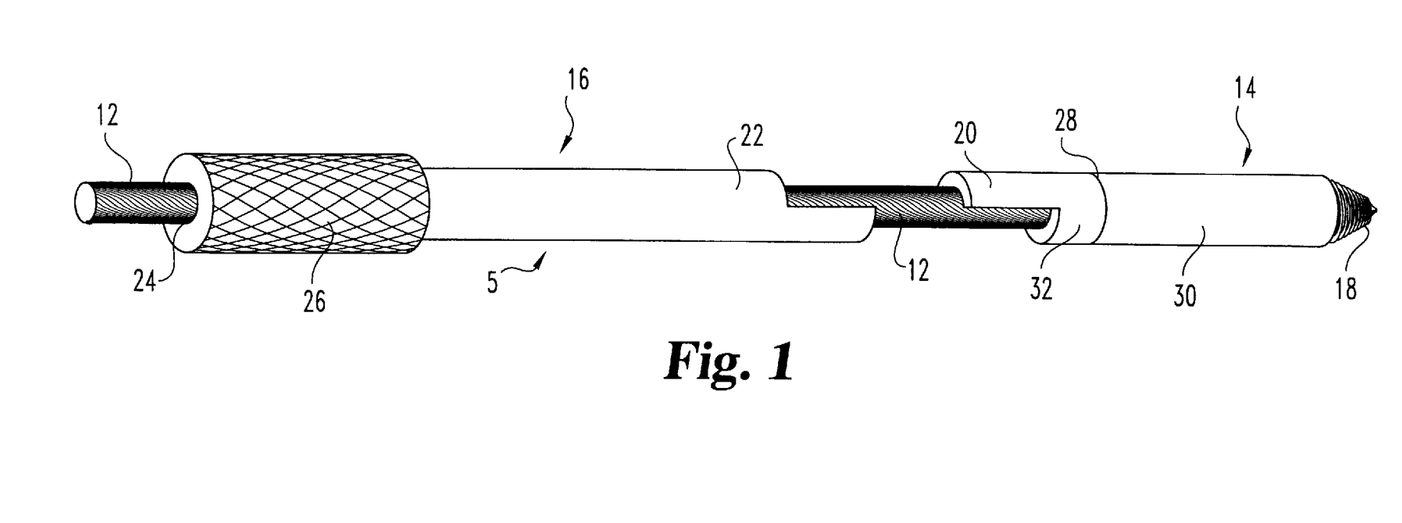
FIG. 1 is a side view of a lesion localizing device according to the preferred embodiment of the invention.

Referring now to FIG. 1, a lesion localizer is shown comprising two rigid elongated components and cable 12. The elongated components comprise distal portions or localizing needle 14 and proximal portion 16 which serves as both a cable sheath and a needle screw driver. Distal portion 14 includes a chamber portion 30 with screw tip 18, and junction portion 32 with interior end 20. Proximal portion includes interior end 22 and proximal end 24. Interior ends 20 and 22 are configured such that when mated, they interfit into a continuous cylinder. Grip end 24 includes hand grip 26 affixed to the outside of the driver 16. In one preferred embodiment grip 26 is made of a rigid material such as stainless steel integral with needle 16, and is knurled.

Localizing needle 14 and driver 16 preferably have an outer diameter between 0.6 and 4.0 mm. Cable 12 preferably has a thickness between 0.2 and 0.8 mm. The driver 16 has a central bore of sufficient size for it to freely rotate and slide along cable 12. Members 14, 16 and cable 12 are constructed of a biocompatible material or, alternatively, are sheathed in a biocompatible material. Lesion localizer 5 is sized such that it can pass longitudinally through the lumen of a guide needle, such as a surgical 14 gauge needle, and is of sufficient length (including cable 12) to reach from the exterior of a patient to the interior lesion site. At a final step in the procedure, upon reaching the lesion site, the localizing needle 14 is anchored near the lesion and driver 16 is then separated from the localizing needle and removed from the cable and guide needle 40.

Figure 2:
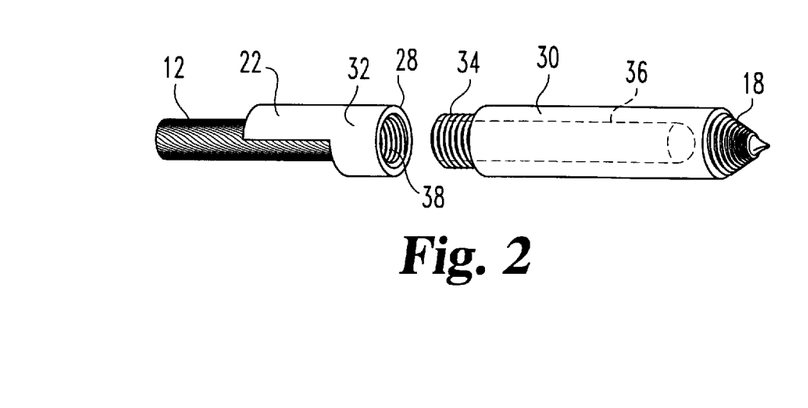
FIG. 2 is an enlarged view of the portion of the device opened for filling with radioactive liquid.

The localizing needle 14 is illustrated in detail in FIG. 2. It comprises two parts, chamber portion 30 and junction portion 32 which are threaded together at joint 28. Chamber portion 30 terminates at its distal end in anchoring screw tip 18. The opposite end is threaded at 34 and is open so that a liquid radioactive agent (technetium, for example) can be placed in chamber 36 therein. Then the chamber is closed and sealed by screwing threads 34 into 38 of junction portion. Screw tip 18 is constructed such that it will screw into bone under application of a torque, to anchor the localizing needle and thereby mark the lesion.

Junction portion 32 comprises interior end 22 and receiver end 38. Interior end 22 is permanently attached to cable 12. Receiver end 38 is threaded to receive the threaded end 34 of chamber portion 32. The threads 34 and 38 are pitched in the same direction as screw tip 18, so that when the localizing needle 14 is rotated and its screw tip engaged with bone during anchoring, chamber portion 30 does not disengage from junction portion 32.

The purpose of the proposed device is to assure accurate localization of bony lesions detectable by radionuclide imaging for subsequent excising surgery. First, the lesion 44 of interest is identified under a persistence scope of nuclear medicine visualization camera/monitor systems, using a bone-avid agent. The overlying skin is prepared and draped in a sterile fashion, and local anesthetic infiltrated along the anticipated track of entry.

Figure 3:
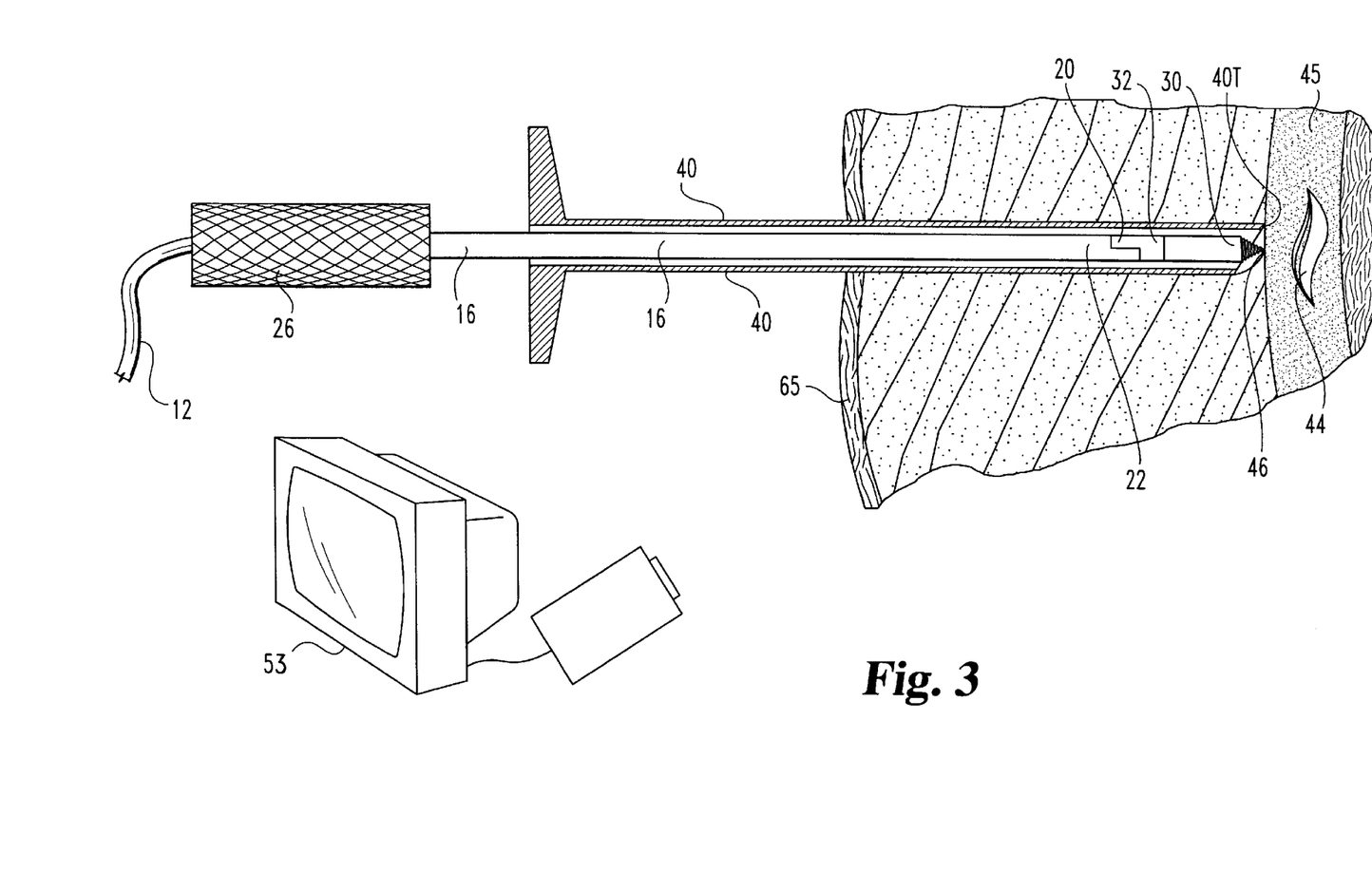
FIG. 3 is a sectional view showing the lesion localizing device inside a guide needle and together inserted into body soft tissue toward a lesion site in bone, illustrating a method of marking a lesion and showing the visualization system schematically on a much reduced scale.
Figure 4:
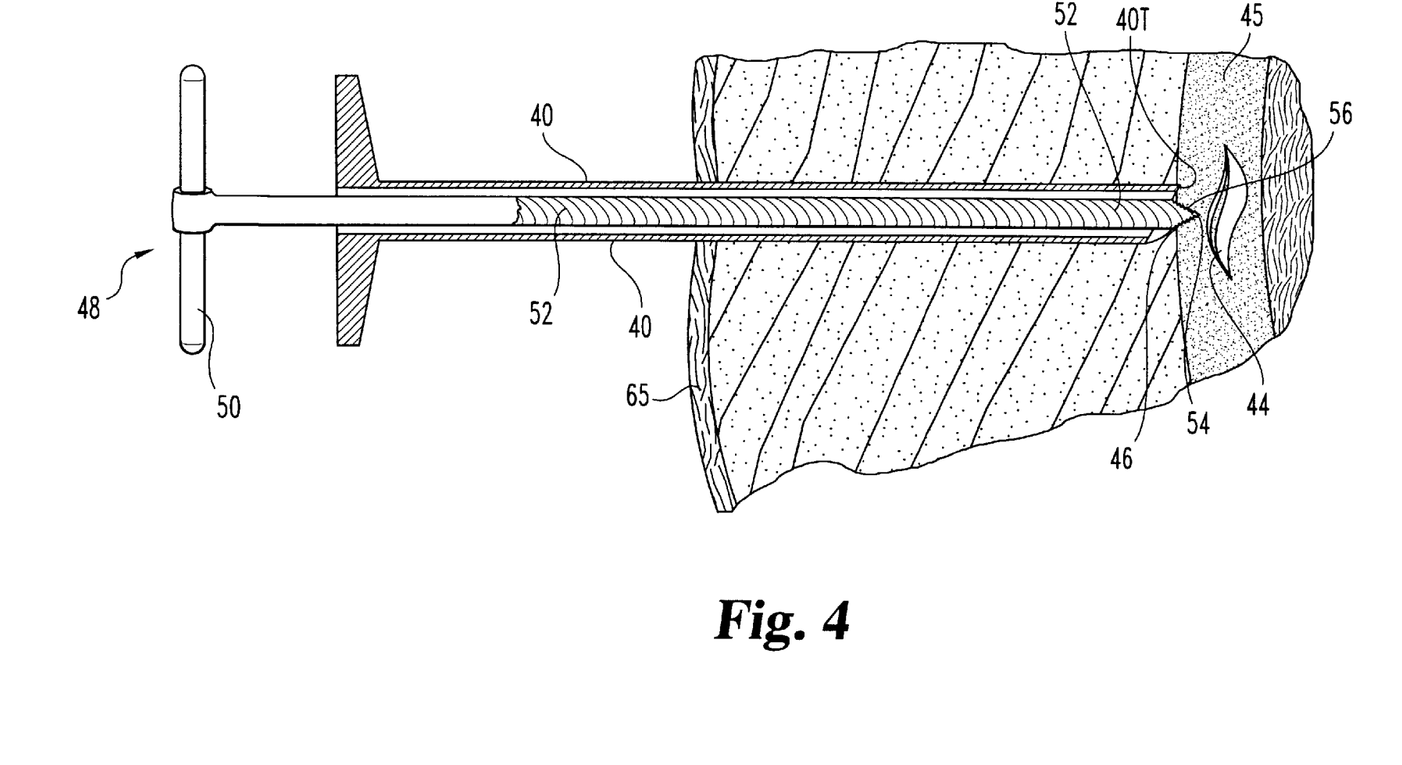
FIG. 4 is a sectional view showing the T-handle drill bit extended through the guide needle to the lesion site.
Figure 5:
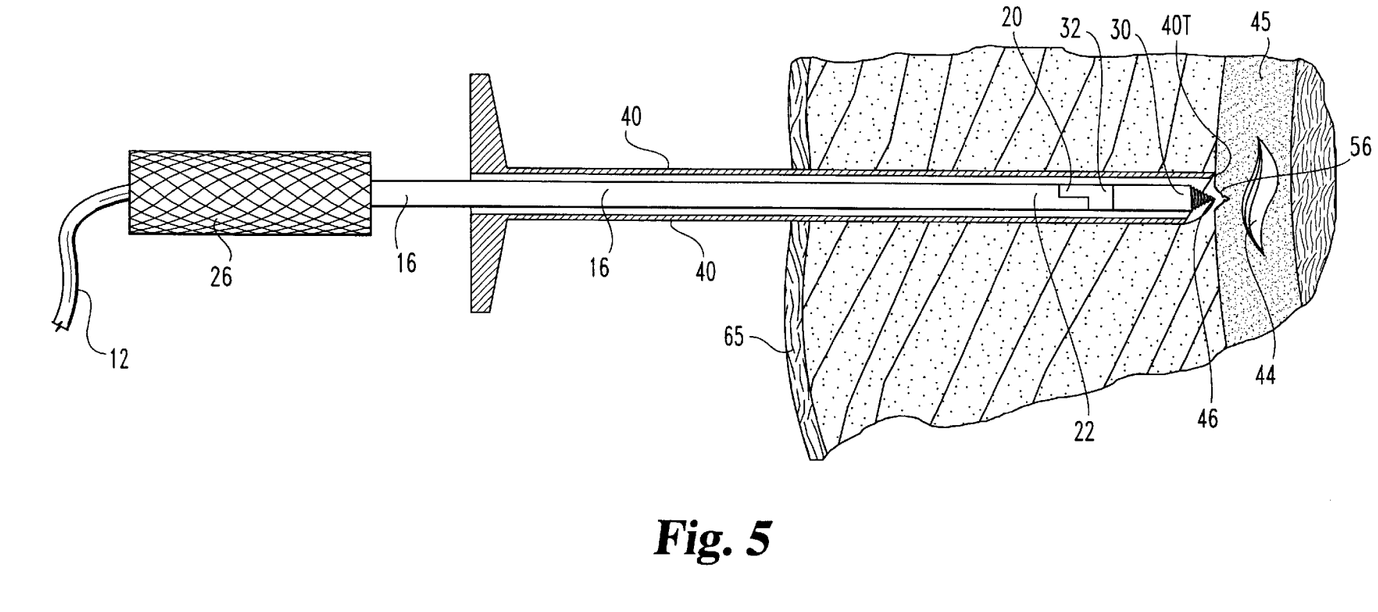
FIG. 5 is a view of the apparatus as in FIG. 3 but where the localizing needle point is screwed into and thereby anchored in the bone at the lesion site
Figure 6:
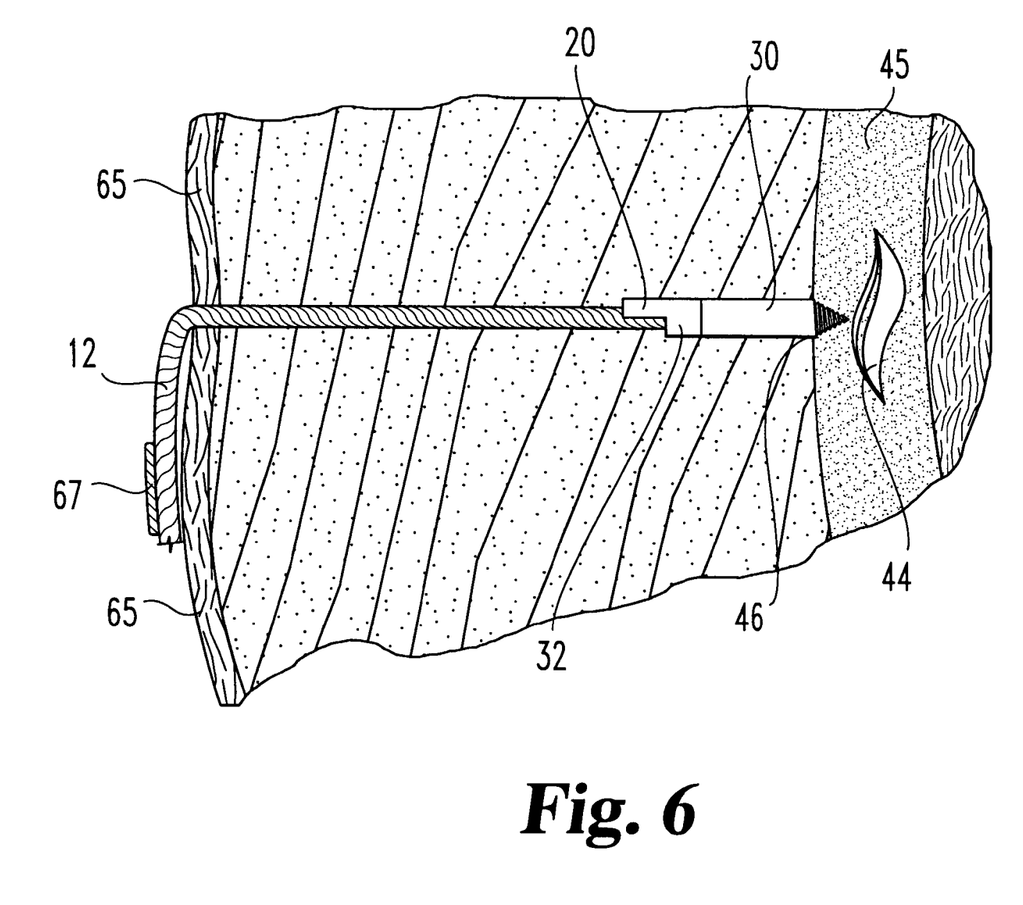
FIG. 6 is a view of the portion of the apparatus remaining after removing the screw driver and guide needle, leaving the localizing needle and cable device marking the lesion site.

The use of the lesion localizer 5 is depicted in FIGS. 3, 5 and 6. FIG. 3 shows the localizing needle 14 of localizer 5 introduced into the lumen 42 of the 14 gauge guiding needle 40. Suitable radioactive material (such as technetium) already installed in chamber 36, makes chamber portion 30 of lesion localizer 5 visible to the visualization system. While observing the screen of the scope 53 on which the lesion 44 is visible due to preferential absorption of an ingested radioactive marker in the lesion, a radiologist can guide lesion localizer 5 toward the lesion. Therefore, while observing the screen, the guide needle 40, with the localizing needle tip 18 at, or immediately behind the guide needle tip, is inserted through the skin and guided toward contact with the bone 45 and marker site 46 proximate the lesion 44. Then the sharp end of the screw tip 18 is advanced slightly out of needle tip 40T to slightly penetrate the bone as close as possible to lesion 44. Then the needle tip 40T is pushed securely against the bone and held firmly enough to remain in place during the rest of the imaging and the marking procedure. Then, while still viewing lesion 44 and localizer chamber portion 30 under nuclear medicine visualization, the localizer is withdrawn from the proximal end of needle 40, while being careful not to disturb the position of needle 40, so that the needle tip 40T remains engaged with the bone at the marker site 46. Starter bit 48 is then inserted into needle 40 as shown in FIG. 4.

In the preferred embodiment, starter bit 48 includes a T-handle, fixed to the proximal end of shaft 52, with drill flutes down the shaft to the sharp drill tip 54. Starter bit 48 is made of sufficiently rigid material, such as stainless steel, such that it can drill a starter hole in bone when torque is applied to T-handle 50. Of course, the shaft of 52 of starter bit 48 is long enough that it can simultaneously protrude from both ends of needle 40.

FIG. 4 depicts the T-handle starter shaft 52 inside needle 40 extending to the marker site 46. The T-handle is used to apply axial force to starter bit 48 along its longitudinal axis, and rotational torque clockwise about its axis to drill a starter hole 56 in the bone cortex at marker site 46. After starter hole 56 is produced, starter bit 48 is withdrawn from needle 40 while again being careful not to disturb the position of the guide needle 40 with respect to marker site 46. Then the lesion localizer components are re-introduced, distal portion with the tip 18 first, and then advanced through needle 40 to starter hole 56, as shown in FIG. 6.

Verification that the needle tip 40T remains properly in place, and the screw tip 18 has entered the starter hole is done by checking the scanner screen and noting the proximity of chamber portion 30 to the lesion 44.

FIG. 5 illustrates the anchoring of lesion localizer 5 to marker site 46. Anchoring is accomplished with the interior ends 20 and 22 interfitting as shown in FIG. 5. Then torque is applied to grip 26 of the driver 16 and transferred through the interfitting ends 20, 22 coupling to the screw tip 18 which is thereby screwed clockwise into the bone cortex at the starter hole 56 (FIG. 4) to a depth of several millimeters, until the screw tip, with the chamber 30, junction 32 and attached cable end, are firmly fixed in position. As the grip surface 26 for the radiologist, is larger than the driver tube 16, and is preferably knurled, this makes it easier for the radiologist to screw tip 18 into the bone. When the radiologist is satisfied with the stability of localizer needle 14, the needle 14 is imaged in two planes. The definitive relationship of the lesion 44 to the small volume of radionuclide in the reservoir chamber 36 should be confirmed prior to withdrawal of the guide needle 40. The longitudinally extending, adjacent flat surfaces of the interior ends 20 and 22, of 32 and 16 enable the driver to turn portion 32 either clockwise to drive screw tip 18 in, or counter-clockwise to remove it, if relocation is needed. Portions 30 and 32 must have been screwed tightly together initially to prevent separating during an effort to unscrew tip 18 from bone. If correct initial location is confirmed, the driver 16 and guiding needle 40 can be withdrawn, leaving the localizing needle 14 (with portions 18, 30 and 32 remaining secured together) fixed to the bony cortex, and the attached cable 12 protruding from the needle wound at the skin. The flexible cable portion protruding outside the skin can be fixed to the skin with a plastic film bandage 67 during transport of the patient elsewhere for procedures outside the imaging department, such as excising surgery at the area marked by the cable. After resection, the bone sample area with the localizing needle 18, 30, 32, in place, should be re-imaged to confirm that the entire radionuclide lesion 44 is contained within the excised sample.

In the later surgery, the surgeon can follow cable 12 to lesion 44. As suggested above, the radioactive marker anchored in the body near the lesion, allows the lesion location to be triangulated by pre-surgery nuclear medicine visualization, when desired.

Figures 7, 8, 9, 10:
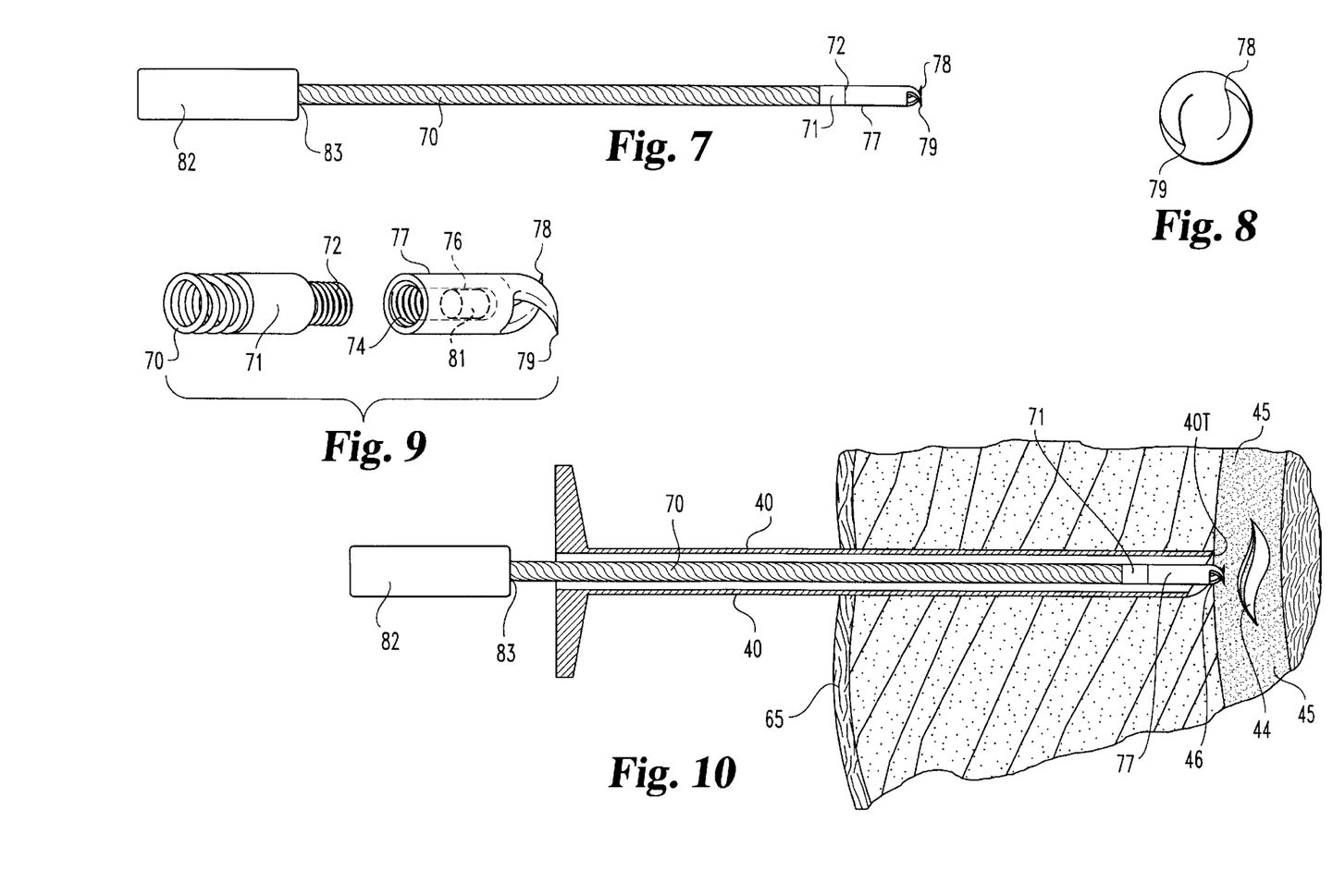
FIG. 7 is a side elevational view of a lesion localizing device according to a second embodiment of the present invention.
FIG. 8 is a distal end view of the localizing needle of FIG. 7.
FIG. 9 is an enlarged fragmentary pictorial view of the distal portion of the second embodiment, ready to be closed after installing the radioactive material.
FIG. 10 is a sectional view of the localizing device installed in a guide needle and being anchored in the bone at the lesion site in the patient's body.

Referring now to FIGS. 7–10 showing the other embodiment of the present invention, the localizer includes a cable which is in the form of a tightly-wound wire coil 70 having a junction member 71 affixed to the distal end thereof, the junction member having a thread 72 at the distal end of it. This thread 72 is received in the threaded open end 74 of chamber 76 of the localizing needle 77. Pointed hooks 78 and 79 are at the distal end of needle 77. An irradiated material 81 (technetium for example) is placed in the chamber 76, following which, the needle end is screwed onto the needle junction 72, closing and sealing the joint at threads 72. A torque device or handle 82 is screwed onto or otherwise non-rotatably attached to the proximal end portion 83 of cable 70. In the use of the device as shown in FIG. 10, and with the bone lesion 44 being visualized on the screen of the persistence scope, and with the tip 72, 71 and cable 70 inside the guide needle 40, the assembly is inserted through the patient's skin 65 and, as the tip assembly 77 is being observed in the scope, it is advanced toward the lesion 44 in the bone, also being observed on the scope. In this example, the tip 40T of the guide needle is pressed securely against the bone and dug into the bone, if possible, at the marker site 46 and held securely. Then the handle 42 is turned at least one-quarter turn about its axis so that the hooked tips 78 and 79 can dig into the bone to anchor the tip into the bone. When securely anchored, the handle 82 can be unscrewed or unpinned from the cable 70 and removed therefrom, following which the guide needle 40 can be removed from the body along the cable 70. Then the portion of the cable protruding from the body at the skin can be taped to the skin as discussed above to remain there until needed later by a surgeon to mark the entry site for surgery.

While the invention has been illustrated and described in detail in the drawings and foregoing description, the same is to be considered as illustrative and not restrictive in character, it being understood that only the preferred embodiment has been shown and described and that all changes and modifications that come with the spirit of the invention are desired to be protected.

What is claimed is:

1. An apparatus to mark the site for treatment of a lesion within tissue, comprising:
   a localizing needle assembly having a rigid proximal portion and having a rigid distal portion having a distal end and having a longitudinal axis;
   one of said portions having a cavity therein containing radioactive material;
   said distal portion and said proximal portion being screwed together to close the cavity; and
   means for anchoring said distal portion in hard tissue.

2. The apparatus of claim 1 wherein said anchoring means comprises a screw tip at the distal end of said distal portion.

3. The apparatus of claim 1 wherein said anchoring means comprises hooks at the distal end of said distal portion.

4. The apparatus of claim 1 and further comprising:
   a cable having a proximal end and a distal end;
   the distal end of the cable being fixed to said proximal portion of said needle assembly.

5. The apparatus of claim 4 and further comprising a torque applicator device mounted to said cable to turn the needle assembly about said longitudinal axis.

6. The apparatus of claim 5 wherein said torque applicator device is removably, but non-rotatably, mounted to the cable.

7. The apparatus of claim 5 wherein said torque applicator device is slidably and rotatably mounted on said cable.

8. The apparatus of claim 7 wherein said torque applicator device and said proximal portion of the needle assembly, have interfittable ends configured to enable bi-directional torque transmission from the torque applicator device to the proximal portion of the needle assembly.

9. The apparatus of claim 4 and wherein:
   the apparatus has a first length from said distal end of the distal portion of the needle assembly to the proximal end of the cable;
   the apparatus further comprising:
   a hollow guide needle having a proximal end and a sharp-tipped distal end for puncturing skin; and
   the length of said guide needle between its ends being less than said first length; and
   the localizing needle assembly and part of the cable residing inside the guide needle and being longitudinally moveable therein relative to the distal end of the guide needle.

10. The assembly of claim 9 and further comprising:
    a torque applicator device mounted to said cable outside the proximal end of said guide needle.

11. The apparatus of claim 1 wherein said distal portion and said proximal portion are screwed together to seal the cavity.

12. An apparatus to mark the site for treatment of a lesion within tissue, comprising:
   a localizing needle assembly having a proximal portion and having a distal portion having a distal end;
   at least one of the portions being adapted to exhibit radioactivity; and means for anchoring said distal portion in tissue;
   wherein one of said portions has a cavity therein to contain radioactive material; and
   said cavity opens at a junction of said portions and said portions are adapted to be separated to open said cavity, and to be securely joined to close said cavity.

13. The apparatus of claim 12 wherein said cavity is in the distal portion adjacent the distal end of said distal portion of the said localizing needle assembly.

14. The apparatus of claim 13 wherein said radioactive material is contained in the cavity.

15. A method for marking the location in tissue of a lesion to be removed from a subject during subsequent surgery, said method comprising the steps of:
   visualizing the lesion on a nuclear medicine monitor;
   placing a localizing needle containing a radiation source in the lumen of a guide needle, with a localizing needle point adjacent the guide needle point and with a cable connected to the localizing needle extending longitudinally in the guide needle lumen and exiting a proximal end of the guide needle;
   advancing the assembly of guide needle and localizing needle through the skin of the subject and observing in real time, the path of travel on the monitor and guiding the needle points toward the lesion;
   contacting hard tissue adjacent the lesion with the point of at least one of the needles;
   applying a rotational torque to the localizing needle to anchor the localizing needle in the hard tissue; and
   removing the guide needle from the cable such that the proximal end of the cable is outside the body of the subject.

16. A method for marking the location in tissue of a lesion to be removed from a subject during subsequent surgery, said method comprising the steps of:
   visualizing the lesion on a nuclear medicine monitor;
   placing a localizing needle containing a radiation source in the lumen of a guide needle, with a localizing needle point adjacent the guide needle point and with a cable connected to the localizing needle extending longitudinally in the guide needle lumen and exiting a proximal end of the guide needle;
   advancing the assembly of guide needle and localizing needle through the skin of the subject and observing in real time, the path of travel on the monitor and guiding the needle points toward the lesion;
   contacting hard tissue adjacent the lesion with the point of at least one of the needles;
   applying a rotational torque to the localizing needle to anchor the localizing needle in the hard tissue; and
   removing the guide needle from the cable such that the proximal end of the cable is outside the body of the subject;
   and further comprising the steps of:
      prior to removing the guide needle, urging a sharp end of the guide needle against hard tissue adjacent the lesion;
      while keeping the guide needle securely engaged with the hard tissue, applying rotational torque to the cable to screw into the hard tissue, two anchor hooks at the tip of the localizing needle to secure it in the hard tissue.

17. A method for marking the location in tissue of a lesion to be removed from a subject during subsequent surgery, said method comprising the steps of:
   visualizing the lesion on a nuclear medicine monitor;
   placing a localizing needle containing a radiation source in the lumen of a guide needle, with a localizing needle point adjacent the guide needle point and with a cable connected to the localizing needle extending longitudinally in the guide needle lumen and exiting a proximal end of the guide needle;
   advancing the assembly of guide needle and localizing needle through the skin of the subject and observing in real time, the path of travel on the monitor and guiding the needle points toward the lesion;
   contacting hard tissue adjacent the lesion with the point of at least one of the needles;
   applying a rotational torque to the localizing needle to anchor the localizing needle in the hard tissue; and
   removing the guide needle from the cable such that the proximal end of the cable is outside the body of the subject;
   and further comprising the steps of:
      prior to removing the guide needle, pushing a sharp point of the guide needle into the hard tissue adjacent the lesion;
      while holding the point of the guide needle securely against and immovably against the hard tissue adjacent the lesion, withdrawing the localizing needle from the guide needle and inserting in the guide needle the sharp point of a drill stylet and engaging the same with the hard tissue;
      while engaging the drill bit of the drill stylet with the hard tissue, applying axial force from the portion of the drill stylet outside the guide needle and torsional force to turn the drill bit into the hard tissue and thereby drill a starter hole in the tissue.

18. The method of claim 17 and further comprising the step of:
   after drilling the starter hole, and while maintaining the guide needle securely affixed against the hard tissue adjacent the lesion, withdrawing the drill stylet and re-inserting the localizing needle so that its point enters the starter hole; and
   driving the localizing needle into the hole while turning the localizing needle tip in the hole and thereby screwing the localizing needle into the starter hole and thereby securing it in the hard tissue adjacent the lesion.

19. The method according to claim 18 and further comprising the step of:
   after screwing the screw tip of the localizing needle into the hard tissue and thereby anchoring it into the hard tissue, removing from the cable, the guide needle and a localizing needle screw driver.

20. The method of claim 19 and further comprising the step of:
   after removing the guide needle, taping to the skin that portion of the cable protruding through the skin toward the proximal end of the cable.

21. The method of claim 18 and further comprising the step of:
   after anchoring the localizing needle point in the hard tissue, visualizing the localizing needle point and lesion in two image planes to confirm the proper location of the localizing needle relative to the lesion, before withdrawing the guide needle.

* * * * *